(12) United States Patent (10) Patent No.: US 8,716,474 B2
Kamimoto et al. (45) Date of Patent: May 6, 2014

(54) METHOD FOR PRODUCING 2,4,6-TRIS(HYDROXYPHENYL)-1,3,5-TRIAZINE COMPOUND

(75) Inventors: Tetsuo Kamimoto, Saitama (JP); Masato Suzuki, Saitama (JP); Yuji Yamazaki, Saitama (JP)

(73) Assignee: Adeka Corporation, Tokyo (JP)

( * ) Notice: Subject to any disclaimer, the term of this patent is extended or adjusted under 35 U.S.C. 154(b) by 128 days.

(21) Appl. No.: 12/995,844

(22) PCT Filed: Jun. 2, 2009

(86) PCT No.: PCT/JP2009/060035
§ 371 (c)(1),
(2), (4) Date: Dec. 2, 2010

(87) PCT Pub. No.: WO2009/148040
PCT Pub. Date: Dec. 10, 2009

(65) Prior Publication Data
US 2011/0087023 A1 Apr. 14, 2011

(30) Foreign Application Priority Data

Jun. 4, 2008 (JP) .................................. 2008-146681
Jun. 4, 2008 (JP) .................................. 2008-146682

(51) Int. Cl.
*C07D 251/24* (2006.01)
*C07D 251/28* (2006.01)

(52) U.S. Cl.
USPC .......................................... 544/216; 544/219

(58) Field of Classification Search
USPC .................................................. 544/216, 219
See application file for complete search history.

(56) References Cited

U.S. PATENT DOCUMENTS

| | | | |
|---|---|---|---|
| 3,244,708 A | 4/1966 | Duennenberger et al. | |
| 5,106,972 A | 4/1992 | Burdeska et al. | |
| 5,726,310 A | 3/1998 | Orban et al. | |
| 5,955,060 A | 9/1999 | Huglin et al. | |
| 6,225,468 B1 | 5/2001 | Gupta et al. | |
| 6,242,598 B1 * | 6/2001 | Stevenson et al. ............. | 544/216 |
| 6,486,316 B1 * | 11/2002 | Gupta et al. .................. | 544/216 |
| 2004/0191191 A1 | 9/2004 | Ehlis et al. | |
| 2007/0178056 A1 | 8/2007 | Mock-Knoblauch et al. | |

FOREIGN PATENT DOCUMENTS

| | | |
|---|---|---|
| EP | 0165608 A2 | 12/1985 |
| GB | 884802 A | 12/1961 |
| JP | 39-4307 A | 4/1964 |
| JP | 42-15700 B1 | 8/1967 |
| JP | 61-24577 A | 2/1986 |

(Continued)

OTHER PUBLICATIONS

European Search Repot issued in European Patent Application No. 09758307.4 dated Mar. 27, 2012.

(Continued)

*Primary Examiner* — Venkataraman Balasubramanian
(74) *Attorney, Agent, or Firm* — Birch, Stewart, Kolasch & Birch, LLP

(57) ABSTRACT

The present invention provides a method of producing 2,4,6-tris(hydroxyphenyl)-1,3,5-triazine compound in which no rapid solidification or the like occurs and generation of by-products is suppressed, thereby enabling to reduce decrease in the yield.

Particularly, the present invention is a method of producing 2,4,6-tris(hydroxyphenyl)-1,3,5-triazine compound represented by the following Formula (1):

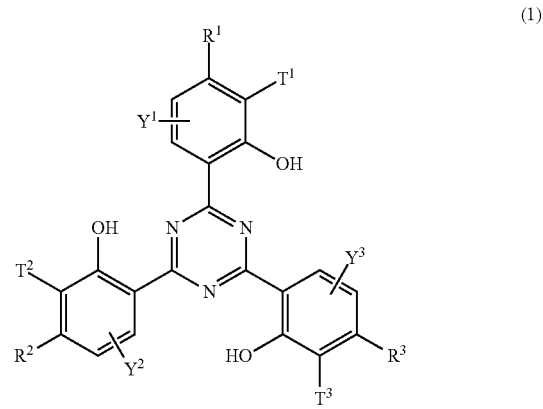

(1)

wherein the reaction between cyanuric halide compound represented by the following Formula (2):

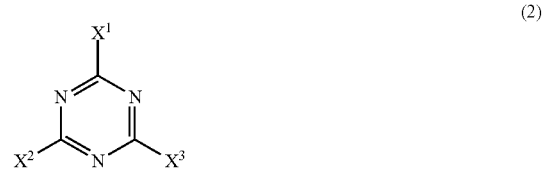

(2)

and hydroxyphenyl compound represented by the following Formula (3):

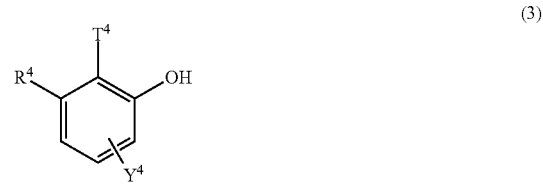

(3)

is carried out by using, as the reaction solvent, a solvent containing sulfolane as the main component in the presence of a Lewis acid at an amount of 0.3 to 0.7 equivalent with respect to 1 equivalent of halogen atom of the cyanuric halide compound represented by the Formula (2), or by using a mixed solvent of inert solvent and cycloalkyl alkyl ether represented by the following Formula (4):

$Z^1-O-Z^2$. (4)

13 Claims, No Drawings

(56) References Cited

FOREIGN PATENT DOCUMENTS

| | | |
|---|---|---|
| JP | 02-292267 A | 12/1990 |
| JP | 9-188666 A | 7/1997 |
| JP | 9-323980 A | 12/1997 |
| JP | 2857219 B2 | 2/1999 |
| JP | 2004-149425 A | 5/2004 |
| JP | 2006-523197 A | 10/2006 |
| JP | 2007-528431 A | 10/2007 |
| JP | 2007-320854 A | 12/2007 |
| WO | WO 2004/085412 A2 | 10/2004 |

OTHER PUBLICATIONS

International Search Report dated Jul. 21, 2009 in Application No. PCT/JP2009/060035.
Chinese Office Action issued in Chinese Patent Application No. 200980120837.7 on Oct. 15, 2012, with English translation.
Chinese Search Report issued in Chinese Patent Application No. 200980120837.7 on Oct. 15, 2012, with English translation.

* cited by examiner

METHOD FOR PRODUCING 2,4,6-TRIS(HYDROXYPHENYL)-1,3,5-TRIAZINE COMPOUND

TECHNICAL FIELD

The present invention relates to a method of producing 2,4,6-tris(hydroxyphenyl)-1,3,5-triazine compound. Particularly, the present invention relates to a method of producing 2,4,6-tris(hydroxyphenyl)-1,3,5-triazine compound in which the compound is easily produced without rapid solidification or the like and generation of by-products is suppressed, thereby enabling to reduce decrease in the yield, and also in which the compound can be synthesized with a low amount of catalyst such that the amount of waste materials can be reduced.

BACKGROUND ART

In recent years, for the purpose of energy saving, weight reduction and the like, flat-panel displays using liquid crystals, plasma or the like have become popular. For these display-related materials, many functional films having optical properties are used. Since these materials are easily deteriorated by UV rays, in order to improve the resistance to light, there are increased demands for an UV-absorbing agent having excellent absorbing capacity in a variety of wavelength regions.

As such UV-absorbing agent, triazine compounds such as 2-(2-hydroxyaryl)-4,6-diaryl-1,3,5-triazine, 2,4-bis(2-hydroxyaryl)-6-aryl-1,3,5-triazine, 2,4,6-tris(2-hydroxyaryl)-1,3,5-triazine and 2,4,6-tris(2,4-dihydroxyaryl)-1,3,5-triazine are known. Particularly, since 2,4,6-tris(2-hydroxyaryl)-1,3,5-triazine and 2,4,6-tris(2,4-dihydroxyaryl)-1,3,5-triazine function as UV-absorbing agent having excellent UV-absorbing capacity in a long-wavelength region, these triazine compounds are expected to be used in an application such as polarizing plate protecting film, where absorbing capacity in a long-wavelength region is required.

In view of this, for the purpose of providing such triazine compound, Patent Documents 1 to 7 disclose methods of producing such triazine compound. For example, Patent Document 1 discloses a production method in which aluminum chloride is used as Lewis acid, and Patent Document 2 discloses a production method in which benzene is used as the solvent.

RELATED ART DOCUMENTS

Patent Documents

Patent Document 1: Japanese Unexamined Patent Application Publication No. H09-323980
Patent Document 2: GB Patent No. 884802 (Description)
Patent Document 3: Japanese Examined Patent Application Publication No. S39-004307
Patent Document 4: Japanese Examined Patent Application Publication No. S42-015700
Patent Document 5: Japanese Unexamined Patent Application Publication No. H09-188666
Patent Document 6: Japanese Unexamined Patent Application Publication (Translation of PCT Application) No. 2006-523197
Patent Document 7: Japanese Patent No. 2857219

DISCLOSURE OF THE INVENTION

Problems to be Solved by the Invention

However, when 2,4,6-tris(hydroxyphenyl)-1,3,5-triazine is produced by the methods described in Patent Documents 1 to 7, there are problems in that the yield of the desired product becomes low due to generation of by-products, that the compound is not easily produced due to rapid solidification of the obtained product, and that the purification is difficult. In addition, in conventional synthesis methods, since a large amount of catalyst is required, which leads to an increased amount of waste materials, there is also a concern relating to environmental issue.

In view of this, an object of the present invention is to provide a method of producing 2,4,6-tris(hydroxyphenyl)-1,3,5-triazine compound in which the compound is easily produced without rapid solidification or the like and generation of by-products is suppressed, thereby enabling to reduce decrease in the yield, and also in which method, the compound can be synthesized with a low amount of catalyst such that the amount of waste materials can be reduced.

Means for Solving the Problems

In order to solve the aforementioned problems, the present inventors intensively studied to discover a method of producing 2,4,6-tris(hydroxyphenyl)-1,3,5-triazine compound in which, by using a solvent containing sulfolane as the main component or a mixed solvent of inert solvent and specific cycloalkyl ether as the reaction solvent in the reaction between cyanuric halide compound and hydroxyphenyl compound, the compound is easily produced without rapid solidification or the like and generation of by-products is suppressed, enabling to reduce decrease in the yield, and also in which method, the compound can be synthesized with a low amount of catalyst such that the amount of waste materials can be reduced, thereby completing the present invention.

That is, the present invention is a method of producing 2,4,6-tris(hydroxyphenyl)-1,3,5-triazine compound represented by the following Formula (1):

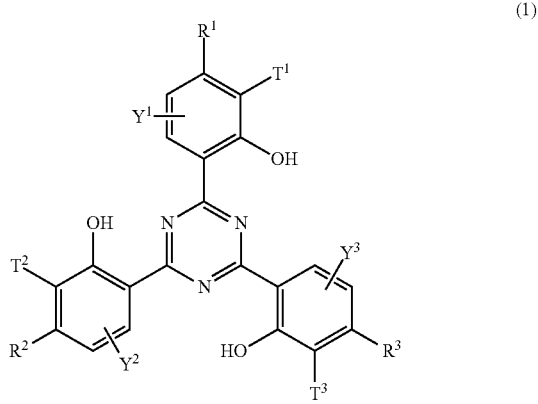

(1)

(wherein,
$R^1$, $R^2$ and $R^3$ each independently represent a hydrogen atom, hydroxyl group or $C_1$-$C_4$ alkyl group;
$T^1$, $T^2$ and $T^3$ each independently represent a hydrogen atom, $C_1$-$C_4$ alkyl group or $C_2$-$C_4$ alkenyl group; and $Y^1$, $Y^2$ and $Y^3$ each independently represent a hydrogen atom or $C_1$-$C_4$ alkyl group),
wherein that the reaction between cyanuric halide compound represented by the following Formula (2):

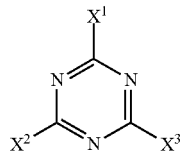

(2)

(wherein,
$X^1$ represents a halogen atom; and
$X^2$ and $X^3$ each independently represent a halogen atom or a substituent by which hydrogen atom of the phenyl ring of the compound represented by the following Formula (3) is substituted) and hydroxyphenyl compound represented by the following Formula (3):

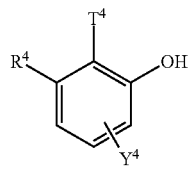

(3)

(wherein,
$R^4$ represents a hydrogen atom, hydroxyl group or $C_1$-$C_4$ alkyl group;
$T^4$ represents a hydrogen atom, $C_1$-$C_4$ alkyl group or $C_2$-$C_4$ alkenyl group; and
$Y^4$ represents a hydrogen atom or $C_1$-$C_4$ alkyl group) is carried out by using, as the reaction solvent, a solvent containing sulfolane as the main component in the presence of a Lewis acid at an amount of 0.3 to 0.7 equivalent with respect to 1 equivalent of halogen atom of the cyanuric halide compound represented by the aforementioned Formula (2), or by using a mixed solvent of inert solvent and cycloalkyl alkyl ether represented by the following Formula (4):

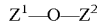 (4)

(wherein,
$Z^1$ represents a cyclopentyl group or cyclohexyl group which optionally has a substituent(s); and
$Z^2$ represents a $C_1$-$C_{10}$ alkyl group or $C_3$-$C_8$ cycloalkyl group which optionally has a substituent (s)).

Further, in the method of producing 2,4,6-tris (hydroxyphenyl)-1,3,5-triazine compound according to the present invention, it is preferred that the aforementioned solvent containing sulfolane as the main component be used and that, in the aforementioned Formulae (1) and (3), $R^1$ to $R^4$ be a hydroxyl group, $T^1$ to $T^4$ be a hydrogen atom or methyl group and $Y^1$ to $Y^4$ be a hydrogen atom.

Still further, in the method of producing 2,4,6-tris(hydroxyphenyl)-1,3,5-triazine compound according to the present invention, it is preferred that the aforementioned solvent containing sulfolane as the main component be used and the aforementioned $T^1$ to $T^4$ be a methyl group. It is also preferred that the aforementioned solvent containing sulfolane as the main component be used and $X^1$ to $X^3$ in the aforementioned Formula (2) be a chlorine atom.

Further, in the method of producing 2,4,6-tris(hydroxyphenyl)-1,3,5-triazine compound according to the present invention, it is preferred that the aforementioned Lewis acid be aluminum trichloride and that the amount of the aforementioned Lewis acid be 0.4 to 0.5 equivalent with respect to 1 equivalent of halogen atom of the aforementioned cyanuric halide compound.

Further, in the method of producing 2,4,6-tris(hydroxyphenyl)-1,3,5-triazine compound according to the present invention, it is preferred that the aforementioned solvent containing sulfolane as the main component be used and that the reaction temperature be 60 to 100° C.

Further, in the method of producing 2,4,6-tris(hydroxyphenyl)-1,3,5-triazine compound according to the present invention, it is preferred that the aforementioned mixed solvent of inert solvent and cycloalkyl alkyl ether represented by the aforementioned Formula (4) be used and that, in the aforementioned Formulae (1) and (3), $R^1$ to $R^4$ be a hydroxyl group, $T^1$ to $T^4$ be a hydrogen atom or methyl group and $Y^1$ to $Y^4$ be a hydrogen atom.

Further, in the method of producing 2,4,6-tris(hydroxyphenyl)-1,3,5-triazine compound according to the present invention, it is preferred that the aforementioned mixed solvent of inert solvent and cycloalkyl alkyl ether represented by the aforementioned Formula (4) be used and the aforementioned $T^1$ to $T^4$ be a methyl group. It is also preferred that the aforementioned mixed solvent of inert solvent and cycloalkyl alkyl ether represented by the aforementioned Formula (4) be used and $X^1$ to $X^3$ in the aforementioned Formula (2) be a chlorine atom.

Still further, in the method of producing 2,4,6-tris(hydroxyphenyl)-1,3,5-triazine compound according to the present invention, it is preferred that the aforementioned inert solvent be at least one selected from the group consisting of chlorobenzene, dichlorobenzene, trichlorobenzene, bromobenzene, dibromobenzene and tribromobenzene; that, in the aforementioned Formula (4), $Z^1$ be a cyclopentyl group and $Z^2$ be a $C_1$-$C_4$ alkyl group; and that the mass ratio of the aforementioned inert solvent to the aforementioned cycloalkyl alkyl ether be 50:50 to 99:1.

Effects of the Invention

By the present invention, it becomes possible to provide a method of producing 2,4,6-tris(hydroxyphenyl)-1,3,5-triazine compound in which the compound is easily produced without rapid solidification or the like and generation of by-products is suppressed, thereby enabling to reduce decrease in the yield, and also in which method, the compound can be synthesized with a low amount of catalyst such that the amount of waste materials can be reduced.

BEST MODE FOR CARRYING OUT THE INVENTION

The embodiments of the present invention will be concretely described below.
First, 2,4,6-tris(hydroxyphenyl)-1,3,5-triazine compound produced in the present invention will be explained.
In the present invention, $R^1$, $R^2$ and $R^3$ in the aforementioned Formula (1) each independently represent a hydrogen atom, hydroxyl group or $C_1$-$C_4$ alkyl group. Examples of the $C_1$-$C_4$ alkyl group in such $R^1$, $R^2$ and $R^3$ include a methyl group, ethyl group, propyl group, isopropyl group, butyl group, isobutyl group, sec-butyl group and tert-butyl group, and the methyl group is particularly preferred.

Further, in the present invention, $T^1$, $T^2$ and $T^3$ in the aforementioned Formula (1) each independently represent a hydrogen atom, $C_1$-$C_4$ alkyl group or $C_2$-$C_4$ alkenyl group. Examples of the $C_1$-$C_4$ alkyl group represented by $T^1$, $T^2$ and $T^3$ include the same groups as those exemplified in the above for the $C_1$-$C_4$ alkyl group in the $R^1$, $R^2$ and $R^3$.

Further, examples of the $C_2$-$C_4$ alkenyl group represented by $T^1$, $T^2$ and $T^3$ in the aforementioned Formula (1) include a vinyl group, propenyl group and butenyl group.

In the present invention, $Y^1$, $Y^2$ and $Y^3$ in the aforementioned Formula (1) each independently represent a hydrogen atom or $C_1$-$C_4$ alkyl group. Examples of the $C_1$-$C_4$ alkyl group represented by $Y^1$, $Y^2$ and $Y^3$ include the same groups as those exemplified in the above for the $C_1$-$C_4$ alkyl group in the $R^1$, $R^2$ and $R^3$.

In the present invention, more specific examples of the 2,4,6-tris(hydroxyphenyl)-1,3,5-triazine compound represented by the aforementioned Formula (1) (hereinafter, also referred to as "the triazine compound") include the following Compounds No. 1 to No. 6. However, in any means, the present invention is not restricted by the following compounds.

Compound No. 1

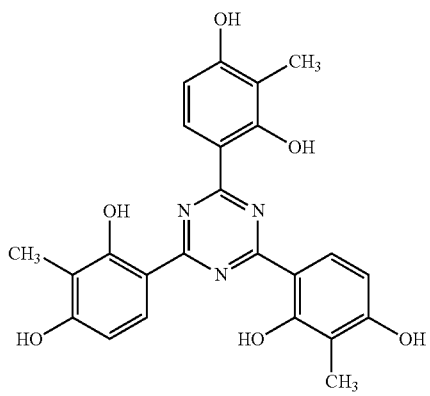

Compound No. 2

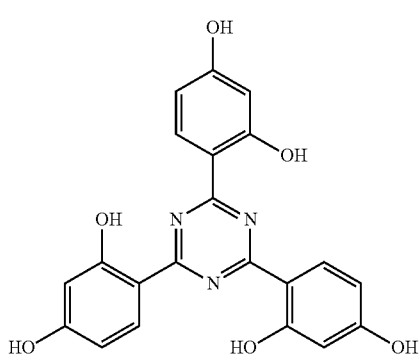

Compound No. 3

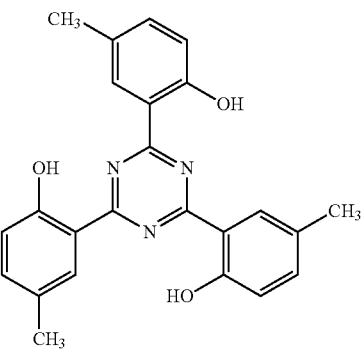

Compound No. 4

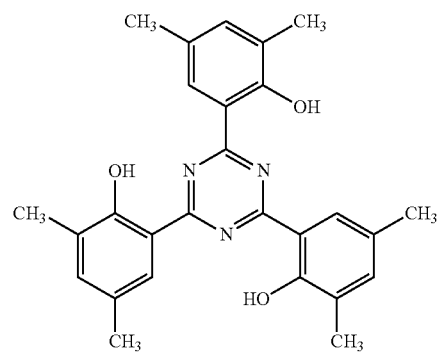

Compound No. 5

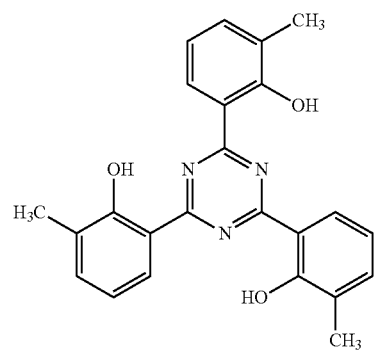

Compound No. 6

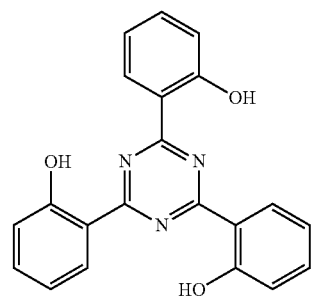

Next, the compounds represented by the aforementioned Formulae (2) and (3), which are the starting materials used in the method of producing the triazine compound according to the present invention, will be explained.

In the present invention, $X^1$ in the aforementioned Formula (2) represents a halogen atom and $X^2$ and $X^3$ each independently represent a halogen atom or a substituent by which hydrogen atom of the phenyl ring of the compound represented by the aforementioned Formula (3) is substituted. Examples of the halogen atom represented by $X^1$, $X^2$ and $X^3$ include fluorine, chlorine, bromine and iodine, and the chlorine is particularly preferred from the standpoint of reactivity and availability.

Further, in the present invention, in the aforementioned Formula (3), $R^4$ represents a hydrogen atom, hydroxyl group or $C_1$-$C_4$ alkyl group; $T^4$ represents a hydrogen atom, $C_1$-$C_4$ alkyl group or $C_2$-$C_4$ alkenyl group; and $Y^4$ represents a hydrogen atom or $C_1$-$C_4$ alkyl group. Examples of the $C_1$-$C_4$ alkyl group represented by $R^4$, $T^4$ and $Y^4$ include the same groups as those exemplified in the above for the $C_1$-$C_4$ alkyl group in the $R^1$ to $R^3$, $T^1$ to $T^3$ or $Y^1$ to $Y^3$.

Further, in the present invention, examples of the $C_2$-$C_4$ alkenyl group represented by $T^4$ in the aforementioned Formula (3) include the same groups as those exemplified in the above for the $C_2$-$C_4$ alkenyl group in the $Y^1$ to $Y^3$.

In the present invention, more specific example of the cyanuric halide compound represented by the aforementioned Formula (2) includes the following Compound No. 7.

Compound No. 7

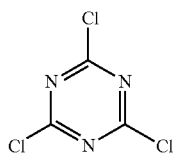

In addition, in the present invention, more specific examples of the hydroxyphenyl compound represented by the aforementioned Formula (3) include the following Compounds No. 8 to No. 13.

Compound No. 8

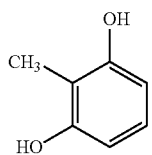

Compound No. 9

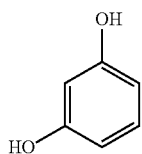

Compound No. 10

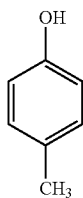

Compound No. 11

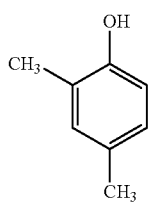

Compound No. 12

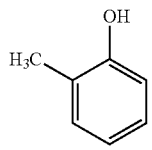

Compound No. 13

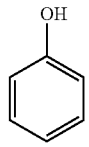

In the present invention, 2,4,6-tris(hydroxyphenyl)-1,3,5-triazine compound of the aforementioned Compounds No. 1 to No. 6 can be produced, for example, by using the aforementioned Compound No. 7 as the cyanuric halide compound and any of the aforementioned Compounds No. 8 to No. 13 as the hydroxyphenyl compound and allowing them to react using as the reaction solvent a solvent containing sulfolane as the main component in the presence of a Lewis acid at an amount of 0.3 to 0.7 equivalent with respect to 1 equivalent of halogen atom of the aforementioned Compound No. 7.

Alternatively, 2,4,6-tris(hydroxyphenyl)-1,3,5-triazine compound of the aforementioned Compounds No. 1 to No. 6 can be produced by allowing the aforementioned Compound No. 7 to react with any of the aforementioned Compounds No. 8 to No. 13 using as the reaction solvent a mixed solvent of inert solvent and cycloalkyl alkyl ether represented by the aforementioned Formula (4).

As the reaction solvent used in the present invention containing sulfolane as the main component, other solvent(s) may be used in combination as long as the reaction solvent contains sulfolane as the main component and the selectivity of the reaction is not impaired. Examples of such other solvent include aromatic solvents such as benzene, toluene, xylene, nitrobenzene, chlorobenzene and dichlorobenzene; aliphatic solvents such as hexane and heptane; ketone-based solvents such as acetone, methyl ethyl ketone, methyl isobutyl ketone and cyclohexanone; ester-based solvents such as ethyl acetate; halogen-based solvents such as chloroform, dichloromethane, trichloroethane and tetrachloroethane; dioxane; diethyl ether; dimethyl sulfoxide; dimethyl formamide; tetrahydrofuran; glyme; and diglyme.

Examples of the inert solvent used in the present invention include aromatic solvents such as benzene, toluene, xylene, nitrobenzene and anisole; aliphatic solvents such as hexane and heptane; aliphatic halogen-based solvents such as chloroform, dichloromethane, trichloroethane and tetrachloroethane; aromatic halogen-based solvents such as chlorobenzene, dichlorobenzene, trichlorobenzene, bromobenzene, dibromobenzene and tribromobenzene; dioxane; diethyl ether; dimethyl sulfoxide; dimethyl formamide; tetrahydrofuran; glyme; diglyme; and sulfolane. Preferred thereamong is a solvent containing at least one selected from the group consisting of aromatic halogen-based solvents such as chlorobenzene, dichlorobenzene, trichlorobenzene, bromobenzene, dibromobenzene and tribromobenzene, and the chlorobenzene is particularly preferred.

In the cycloalkyl alkyl ether which is used in the present invention and represented by the aforementioned Formula (4), $Z^1$ represents a cyclopentyl group or cyclohexyl group which optionally has a substituent(s). Examples of the substituent include $C_1$-$C_4$ alkyl groups, $C_1$-$C_4$ alkoxy groups, $C_1$-$C_4$ alkylthio groups and halogen atoms, and thereamong, a $C_1$-$C_4$ alkyl group is preferred and a methyl group or ethyl group is more preferred.

Specific examples of the cyclopentyl group or cyclohexyl group which is represented by the aforementioned $Z^1$ and optionally has a substituent(s) include cyclopentyl groups or cyclohexyl groups; alkyl-cyclopentyl groups or alkyl-cyclohexyl groups such as 2-methyl-cyclopentyl group, 3-sec-butyl-cyclopentyl group, 3-ethyl-cyclohexyl group and 2-tert-butyl-cyclohexyl group; alkoxy-cyclopentyl groups or alkoxy-cyclohexyl groups such as 3-methoxy-cyclopentyl group, 2-sec-butoxy-cyclopentyl group, 3-ethoxy-cyclohexyl group and 3-tert-butoxy-cyclohexyl group; alkylthio-cyclopentyl groups or alkylthio-cyclohexyl groups such as 3-methylthio-cyclopentyl group, 2-sec-butylthio-cyclopentyl group, 3-ethylthio-cyclohexyl group and 3-tert-butylthio-cyclohexyl group; and halogenated cyclopentyl groups or halogenated cyclohexyl groups such as 2-chloro-cyclopentyl group, 3-chloro-cyclopentyl group, 2-bromo-cyclohexyl group and 3-bromo-cyclohexyl group. Preferred thereamong are cyclopentyl group, cyclohexyl group, 2-methyl-cyclopentyl group and 3-ethyl-cyclohexyl group, and cyclopentyl group is particularly preferred.

In the cycloalkyl alkyl ether which is used in the present invention and represented by the aforementioned Formula (4), $Z^2$ represents a $C_1$-$C_{10}$ alkyl group or $C_3$-$C_8$ cycloalkyl group which optionally has a substituent(s). Examples of the substituent include $C_1$-$C_4$ alkyl groups, $C_1$-$C_4$ alkoxy groups, $C_1$-$C_4$ alkylthio groups and halogen atoms, and thereamong, a $C_1$-$C_4$ alkyl group is preferred and a methyl group or ethyl group is more preferred.

Specific examples of the $C_1$-$C_{10}$ alkyl group or $C_3$-$C_8$ cycloalkyl group which is represented by the aforementioned $Z^2$ and optionally has a substituent(s) include $C_1$-$C_{10}$ alkyl groups such as methyl group, ethyl group, n-propyl group, isopropyl group, n-butyl group, sec-butyl group, tert-butyl group, n-pentyl group, neopentyl group, n-hexyl group, n-heptyl group, n-octyl group, n-nonyl group and n-decyl group; $C_3$-$C_8$ cycloalkyl groups such as cyclopropyl group, cyclobutyl group, cyclopentyl group, cyclohexyl group, cycloheptyl group and cyclooctyl group; alkoxyalkyl groups such as methoxymethyl group, 1-methoxyethyl group, 2-ethoxy-tert-butyl group and 2-ethoxy-n-hexyl group; alkoxy-cycloalkyl groups such as 2-methoxy-cyclopropyl group and 3-ethoxy-cyclohexyl group; alkylthio-alkyl groups such as methylthiomethyl group, 1-methylthioethyl group, 2-methylthio-tert-butyl group and 4-methylthio-n-hexyl group; alkylthio-cycloalkyl groups such as 2-methylthio-cyclopropyl group and 3-ethylthio-cyclohexyl group; halogenated alkyl groups such as chloromethyl group, bromomethyl group, 1-chloroethyl group, 2-bromo-tert-butyl group and 2-chloro-n-hexyl group; and halogenated cycloalkyl groups such as 2-chloro-cyclopropyl group and 3-bromo-cyclohexyl group.

Further, the mass ratio between the inert solvent and cycloalkyl alkyl ether used in the present invention is preferably 50:50 to 99:1 (the former:the latter), more preferably 80:20 to 99:1, and particularly preferably 90:10 to 99:1. In cases where the mass ratio of cycloalkyl alkyl ether is less than 1 wt %, the effects of the present invention are lost and a drastic exothermic reaction occurs making the reaction uncontrollable, and at the same time, stirring may become difficult due to generation of viscous matter. In contrast, when the mass ratio of cycloalkyl alkyl ether exceeds 50 wt %, there maybe an increased generation of by-products, which may decrease the yield. Therefore, such mass ratios are not preferred.

The reaction solvent which is used in the present invention and contains sulfolane as the main component is used, with respect to the theoretical yield, preferably at an amount of not less than 200 parts by mass, more preferably at an amount of 200 to 500 parts by mass, and particularly preferably, from the economical standpoint, at an amount of 200 parts by mass. An amount less than 200 parts by mass is not preferred since there may be a problem, for example, that the reaction time becomes extended due to insufficient dissolution of a Lewis acid such as aluminum trichloride or that the reaction solution becomes highly viscous and loses fluidity, thereby damaging the stirrer and/or making it impossible to be loaded into the treatment solution.

The total amount of the inert solvent and cycloalkyl alkyl ether solvent used in the present invention is, with respect to 100 parts by mass of the theoretical yield, preferably at an amount of 100 to 2,000 parts by mass, more preferably at an amount of 300 to 1,500 parts by mass, and particularly preferably at an amount of 500 to 1,000 parts by mass. An amount less than 100 parts by mass is not preferred since there may be a problem, for example, that the raw materials cannot be sufficiently dissolved, causing a heterogeneous reaction and extended reaction time, or that, in order to dissolve the raw materials uniformly, the reaction temperature becomes high and by-products are generated in a large amount. On the other hand, an amount greater than 2,000 parts by mass is not preferred since, even at such an amount, the effect of further improving the desired performance is hardly attained while the cost becomes inflated.

Further, in cases where a solvent containing sulfolane as the main component is used, it is preferred that the addition of the hydroxyphenyl compound represented by Formula (3) in the production method according to the present invention be carried out, since it tends to be difficult to control the reaction rate (and temperature) in the reaction performed by simultaneous addition thereof with the cyanuric halide compound represented by Formula (2), by dissolving the hydroxyphenyl compound into the same solvent as the reaction solvent in advance and subsequently dropping the thus obtained hydroxyphenyl compound solution into the reaction solution. The amount of the solvent used is not particularly restricted; however, it is, with respect to the theoretical yield, preferably at an amount of not less than 150 parts by mass, more preferably 150 to 300 parts by mass, and particularly preferably, from the economical standpoint, at an amount of 150 parts by mass. An amount less than 150 parts by mass is not preferred since there may be a problem, for example, that the dissolution of the hydroxyphenyl-based raw material becomes difficult or that the reaction solution becomes highly viscous to lose fluidity, thereby damaging the stirrer or making it impossible to be loaded into the treatment solution.

In cases where a solvent containing sulfolane as the main component is used, the reaction temperature is preferably 60 to 100° C., more preferably 70 to 80° C. At a temperature lower than 60° C., since the initial reaction is slow and the product becomes solidified due to drastic exothermic reaction in the middle phase of the reaction, it tends to become difficult to produce the desired compound, and at a temperature higher than 100° C., the product may become colored or the selectivity may be lowered, thereby increasing the amount of by-products; therefore, such temperatures are not preferred.

In cases where a mixed solvent of inert solvent and cycloalkyl alkyl ether represented by the aforementioned Formula (4) is used, the reaction temperature is preferably 20 to 120° C., more preferably 40 to 80° C. At a temperature lower than 20° C., since the initial reaction is slow and the product becomes solidified due to the drastic exothermic reaction in the middle phase of the reaction, it tends to become difficult to produce the desired compound, and at a temperature higher than 120° C., the product may become colored or the selectivity may be lowered, thereby increasing the amount of by-products; therefore, such temperatures are not preferred.

The pressure during the reaction is preferably normal pressure at which the reaction solvent is not evaporated or the reaction is preferably carried out under an increased pressure. Normal pressure is particularly preferred since the reaction can be carried out using a simple device.

In the present invention, a Lewis acid catalyst is preferably used as the reaction catalyst. Examples of the Lewis acid include aluminum halide, boron halide, tin halide, zinc halide, lead halide, manganese halide, magnesium halide, copper halide, titanium halide, alkylaluminum halide, gallium halide, iron halide, arsenic halide, antimony halide, thallium halide, zirconium halide, tungsten halide, molybdenum halide, niobium halide and a mixture thereof. Specific examples include aluminum trichloride ($AlCl_3$), aluminum tribromide, trimethyl aluminum, boron trifluoride, boron trichloride, zinc dichloride, titanium tetrachloride, tin dichloride, tin tetrachloride, ferric chloride and a mixture thereof. Thereamong, it is preferred to use aluminum trichloride from the standpoint of catalyst activity, cost and handling.

In conventional Friedel-Crafts reaction, a Lewis acid is generally used at an amount of not less than 1 equivalent with respect to 1 equivalent of halogen atom of the cyanuric halide compound; however, in the present invention, when using a solvent containing sulfolane as the main component, the amount of the Lewis acid is 0.3 to 0.7 equivalent with respect to 1 equivalent of halogen atom of the cyanuric halide compound, thereby enabling to obtain the desired product at a high purity. Further, taking the moisture absorption of the Lewis acid which is the catalyst into consideration, it is preferred that the Lewis acid be used at an amount of 0.4 to 0.5 equivalent. An amount of less than 0.3 equivalent is not preferred since the reaction activity becomes too low, while it is not industrially preferred to use the Lewis acid at an amount exceeding 0.7 equivalent since it unnecessarily increases the waste materials.

In cases where a mixed solvent of inert solvent and cycloalkyl alkyl ether represented by the aforementioned Formula (4) is used, the Lewis acid is used, with respect to the cyanuric halide compound represented by the aforementioned Formula (2), at an amount of 0.1 to 10 equivalents, preferably at an amount of 1 to 6 equivalents. An amount of less than 0.1 equivalent is not preferred since the reaction activity may become too low, while it is not also preferred to use the Lewis acid at an amount exceeding 10 equivalents since it unnecessarily increases the waste materials.

In cases where a mixed solvent of inert solvent and cycloalkyl alkyl ether represented by the aforementioned Formula (4) is used, the procedure for producing 2,4,6-tris(hydroxyphenyl)-1,3,5-triazine compound is not particularly restricted in the present invention; however, examples thereof include: a) a method in which hydroxyphenyl compound/solvent is dropped into cyanuric halide compound/solvent; b) a method in which cyanuric halide compound/solvent is dropped into hydroxyphenyl compound/solvent; and c) a method in which cyanuric halide compound and hydroxyphenyl compound are simultaneously added to the solvent and allowed to react. Preferred thereamong is the method of c) a method in which cyanuric halide and hydroxyphenyl compound are simultaneously added, since it tends to produce the desired product at a high yield.

The triazine compound obtained in the present invention can be suitably used as a UV-absorbing agent in stabilization of various organic substances or synthetic resins, or as an intermediate of the UV-absorbing agent. Particularly, the triazine compound obtained in the present invention can be suitably used as an intermediate when producing a hydroxytriazine compound derivative.

Examples of the aforementioned synthetic resin include α-olefin polymers or ethylene-vinyl acetate copolymers such as polypropylene, high-density polyethylene, low-density polyethylene, linear low-density polyethylene, polybutene-1 and poly-4-methylpentene; polyolefins and copolymers thereof such as ethylene-propylene copolymers; halogen-containing resins such as polyvinyl chloride, polyvinylidene chloride, polyethylene chloride, polypropylene chloride, polyvinylidene fluoride, chlorinated rubber, vinyl chloride-vinyl acetate copolymer, vinyl chloride-ethylene copolymer, vinyl chloride-vinylidene chloride copolymer, vinyl chloride-vinylidene chloride-vinyl acetate terpolymer, vinyl chloride-acrylate copolymer, vinyl chloride-maleate copolymer and vinyl chloride-cyclohexylmaleimide copolymer; copolymers (for example, AS resin, ABS resin, MBS resin and heat-resistant ABS resin) between petroleum resin, coumarone resin, polystyrene, polyvinyl acetate, acryl, styrene and/or a-methyl styrene and other monomer (for example, maleic anhydride, phenyl maleimide, methyl methacrylate, butadiene, acrylonitrile); acrylate-based resins such as polymethyl acrylate and polymethyl metacrylate; vinyl-based resins such as polyvinyl alcohol, polyvinyl formal and polyvinyl butyral; polyester-based resins such as polyethylene terephthalate, polytetramethylene terephthalate and polyethylene naphthalate; cellulose ester-based resins such as cellulose triacetate and cellulose acetate butyrate; polyamide resins such as polyphenylene oxide, polycaprolactam and polyhexamethylene adipamide; thermoplastic resins such as polycarbonate, branched polycarbonate, polyacetal, polyphenylene sulfide, cycloolefin, norbornene and polyurethane and a mixture thereof; and thermosetting resins such as phenol resin, urea resin, melamine resin, epoxy resin and unsaturated polyester resin. Further, the aforementioned synthetic resin may be an elastomer such as isoprene rubber, butadiene rubber, acrylonitrile-butadiene copolymer rubber or styrene-butadiene copolymer rubber. Particularly, in resins having excellent transparency such as polycarbonate-based resins, polyethylene terephthalate-based resins, polyethylene naphthalate-based resins, cellulose ester-based resins, acrylate-based resins, cycloolefin-based resins, polystyrene-based resins and norbornene-based resins, the aforementioned synthetic resin can be suitably used not only for stabilization of the very resin in which the synthetic resin is blended, but also for preventing deterioration of other members by UV rays.

There is no particular restriction on the method of blending the triazine compound obtained in the present invention into the synthetic resin. The optimum blending method is appropriately selected, depending on the melt viscosity, the presence or absence of other compounding agent(s), the type thereof and the like, from methods in which the triazine compound and synthetic resin are liquefied using a solvent, such as a melt-kneading method by an extruder or the like and a casting method; and resin polymerization methods such as one in which the triazine compound is added at the time of or immediately after polymerization, such as emulsion polymerization, suspension polymerization solution polymerization or the like, one in which the triazine compound is mixed with other additive component(s) in advance and granulated, and one in which the triazine compound is melt-kneaded at a high concentration into the resin and master-batched before being blended into the resin.

Examples of the aforementioned other additive component include phenolic antioxidant, phosphorus antioxidant, thioether-based antioxidant, other UV-absorbing agents, hindered amine-based lightstabilizer, plasticizer, nucleating agent, flame-retardant, flame-retardant aid, heavy-metal inactivator, antistatic agent, lubricant, metallic soap, hydrotalcite, pigment, dye, antibacterial agent, fungicide, rodent repellent, surfactant and filler.

Examples of the aforementioned phenolic antioxidant include 2,6-di-tert-butyl-p-cresol, 2,6-diphenyl-4-octadecyloxyphenol, distearyl(3,5-di-tert-butyl-4-hydroxybenzyl) phosphonate, 1,6-hexamethylenebis[(3,5-di-tert-butyl-4-hydroxyphenyl) propionic acid amide], 4,4'-thiobis(6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis (4,6-di-tert-butylphenol), 2,2'-ethylidenebis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl) isocyanurate, 1,3,5-tris(3,5-di-tert-butyl-4-hydroxybenzyl) isocyanurate, 1,3,5-tris(3,5-di-tert-butyl-4-hydroxybenzyl) -2,4,6-trimethylbenzene, 2-tert-butyl-4-methyl-6-(2-acryloyloxy-3-tert-butyl-5-methylbenzyl) phenol, stearyl(3,5-di-tert-butyl-4-hydroxyphenyl)propionate, thiodiethylene glycol bis[(3,5-di-tert-butyl-4-hydroxyphenyl) propionate], 1,6-hexamethylenebis[(3,5-di-tert-butyl-4-hydroxyphenyl) propionate], bis[3,3-bis(4-hydroxy-3-tert-butylphenyl)butyric acid]glycol ester, bis[2-tert-butyl-4-methyl-6-(2-hydroxy-3-tert-butyl-5-methylbenzyl) phenyl] terephthalate, 1,3,5-tris[(3,5-di-tert-butyl-4-hydroxyphenyl) propionyloxyethyl]isocyanurate, 3,9-bis[1,1-dimethyl-2-{ (3-tert-butyl-4-hydroxy-5-methylphenyl) propionyloxy}ethyl]-2,4,8,10-tetraoxaspiro[5.5] undecane, triethylene glycol bis[(3-tert-butyl-4-hydroxy-5-methylphenyl) propionate] and tocophenol. The phenolic antioxidant is used preferably at an amount of 0.001 to 10 parts by mass, more preferably at an amount of 0.05 to 5 parts by mass, with respect to 100 parts by mass of the resin.

Examples of the aforementioned phosphorus antioxidant include trisnonylphenyl phosphite, tris[2-tert-butyl-4-(3-tert-butyl-4-hydroxy-5-methylphenylthio)-5-methylphenyl] phosphite, tridecyl phosphite, octyl diphenyl phosphite, di(decyl)monophenyl phosphite, di(tridecyl)pentaerythritol diphosphite, di(nonylphenyl)pentaerythritol diphosphite, bis (2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra (tridecyl)isopropylidene diphenol diphosphite, tetra(tridecyl)-4,4'-n-butylidenebis (2-tert-butyl-5-methylphenol) diphosphite, hexa(tridecyl)-1,1,3-tris(2-methyl-4-hydroxy-5-tert-butylphenyl)butane triphosphite, tetrakis(2,4-di-tert-butylphenyl)biphenylene diphosphonite, 9,10-dihydro-9-oxa-10-phosphaphenanthrene-10-oxide, 2,2'-methylenebis (4,6-tert-butylphenyl)-2-ethylhexylphosphite, 2,2'-methylenebis(4,6-tert-butylphenyl)-octadecyl phosphite, 2,2'-ethylidenebis(4,6-di-tert-butylphenyl)fluorophosphite, tris(2-[(2,4,8,10-tetrakis-tert-butyldibenzo[d,f][1,3,2] dioxaphosphepin-6-yl)oxy]ethyl)amine, and phosphite of 2-ethyl-2-butylpropylene glycol and 2,4,6-tri-tert-butylphenol. The phosphorus antioxidant is used at an amount of 0.001 to 10 parts by mass, more preferably at an amount of 0.01 to 5 parts by mass, with respect to 100 parts by mass of the resin.

Examples of the aforementioned thioether-based antioxidant include dialkyl thiodipropionates such as dilauryl thiodipropionate, dimyristyl thiodipropionate and distearyl thiodipropionate; and (β-alkyl mercaptopropionate esters of polyols such as pentaerythritol tetra (β-dodecyl mercaptopropionate). The thioether-based antioxidant is used at an amount of 0.001 to 10 parts by mass, more preferably at an amount of 0.01 to 5 parts by mass, with respect to 100 parts by mass of the resin.

Examples of the aforementioned other UV-absorbing agent include benzotriazole-based UV-absorbing agents, other triazine-based UV-absorbing agents and benzophenone-based UV-absorbing agents. These other UV-absorbing agents are used preferably at an amount of 0.01 to 10 parts by mass, more preferably at an amount of 0.05 to 5 parts by mass, with respect to 100 parts by mass of the resin.

Examples of the aforementioned benzotriazole-based UV-absorbing agent include 2-(2'-hydroxyphenyl)benzotriazoles such as 2-(2'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl)benzotriazole, 2-(2'-hydroxy-3',5'-dicumylphenyl)benzotriazole, 2-(2'-hydroxy-3'-tert-butyl-5-carboxyphenyl) benzotriazole and 2,2'-methylenebis(4-tert-octyl-6-benzotriazolyl)phenol.

Examples of the aforementioned other triazine-based UV-absorbing agent include triaryltriazines such as 2-(2-hydroxy-4-octoxyphenyl)-4,6-bis(2,4-dimethylphenyl)-s-triazine, 2-(2-hydroxy-4-hexyloxyphenyl)-4,6-diphenyl-s-triazine, 2-(2-hydroxy-4-propoxy-5-methylphenyl)-4,6-bis (2,4-dimethylphenyl)-s-triazine, 2-[2-hydroxy-4-(3-dodecyloxy-2-hydroxypropyloxy)phenyl]-4,6-bis (2,4-dimethylphenyl)-s-triazine, 2-[2-hydroxy-4-(3-tridecyloxy-2-hydroxypropyloxy)phenyl]-4,6-bis (2,4-dimethylphenyl)-s-triazine, 2-[2-hydroxy-4-[3-(2-ethylhexyloxy)-2-hydroxypropyloxy]phenyl]-4,6-bis(2,4-dimethylphenyl)-s-triazine, 2-(2-hydroxy-4-hexyloxyphenyl)-4,6-dibiphenyl-s-triazine, 2-[2-hydroxy-4-[1-(i-octyloxycarbonyl)ethyloxy] phenyl]-4,6-dibiphenyl-s-triazine, 2,4-bis(2-hydroxy-4-octoxyphenyl)-6-(2,4-dimethylphenyl)-s-triazine, 2,4-bis(4-butoxy-2-hydroxyphenyl)-6-(2,4-dibutoxyphenyl)-s-triazine and 2,4,6-tris(2-hydroxy-4-octoxyphenyl)-s-triazine.

Examples of the aforementioned benzophenone-based UV-absorbing agent include 2-hydroxy benzophenones such as 2,4-dihydroxy benzophenone, 2-hydroxy-4-methoxy benzophenone, 2-hydroxy-4-octoxy benzophenone and 5,5'-methylenebis(2-hydroxy-4-methoxy benzophenone).

Examples of the aforementioned hindered amine-based lightstabilizer include 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, bis(1,2,2,6,6-pentamethyl-4-piperidyl) sebacate, tetrakis(2,2,6,6-tetramethyl-4-piperidylbutane tetracarboxylate, tetrakis(1,2,2,6,6-pentamethyl-4-piperidylbutane tetracarboxylate, bis(2,2,6,6-tetramethyl-4-piperidyl) di(tridecyl)-1,2,3,4-butane tetracarboxylate, bis(1,2,2,6,6-pentamethyl-4-piperidyl) di(tridecyl)-1,2,3,4-butane tetracarboxylate, bis(1,2,2,6,6-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/dibromoethane polycondensate, 1,6-bis (2,2,6,6-tetramethyl-4-piperidylamino)hexane/2,4-dichloro-6-morphorino-s-triazine polycondensate, 1,6-bis(2,2,6,6-tetramethyl-4-piperidylamino)hexane/2,4-dichloro-6-tert-octylamino-s-triazine polycondensate, and hindered amine compounds such as 1,5,8,12-tetrakis[2,4-bis(N-butyl-N-(2,2,6,6-tetramethyl-4-piperidyl)amino)-s-triazine-6-yl]-1,5,8, 12-tetraazadodecane, 1,5,8,12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2, 2,6,6-tetramethyl-4-piperidyl)amino)-s-triazine-6-ylamino undecane and 1,6,11-tris[2,4-bis(N-butyl-N-(1,2,2,6,6-pentamethyl-4-piperidyl)amino)-s-triazine-6-ylamino undecane. The hindered amine-based lightstabilizer is used at an amount of 0.001 to 10 parts by mass, more preferably at an amount of 0.01 to 5 parts by mass, with respect to 100 parts by mass of the resin.

As the aforementioned plasticizer, a variety of known plasticizers can be used depending on the applied resin. For instance, examples of ester-based plasticizer include dibasic acids such as phthalic acid, naphthalene dicarboxylic acid, succinic acid, glutaric acid, adipic acid and maleic acid; alkyl alcohols such as octanol, isononyl alcohol, lauryl alcohol and stearyl alcohol; and diester compounds of ether alcohol and the like such as diethylene glycol monobutylether. Examples of polyester-based plasticizer include polyesters consisting of the aforementioned dibasic acid and a glycol such as ethylene glycol, propylene glycol, butanediol, neopentyl glycol or hexanediol, as well as such polyesters whose terminal is capped by the aforementioned monoalcohol or a monocarboxylic acid compound such as propionic acid, octyl acid or benzoic acid. Examples of polyether plasticizer include polyethers such as polyethylene glycol and polypropylene glycol, and examples of polyether-ester-based plasticizer include polyethers such as polyethylene glycol and polypropylene glycol, as well as polyesters of the aforementioned dibasic acids.

Examples of the aforementioned nucleating agent include metal salts of aromatic acid such as sodium benzoate and p-(tert-butyl) aluminum benzoate; metal salts of phosphoric ester such as sodium-2,2'-bis(4,6-di-tert-butylphenyl) phosphate, lithium-2,2'-bis(4,6-di-tert-butylphenyl) phosphate and aluminum-hydroxy-bis(2,2'-bis (4,6-di-tert-butylphenyl) phosphate); sorbitols such as dibenzylidene sorbitol, bis(4-methylbenzylidene)sorbitol and bis(3,4-dimethylbenzylidene)sorbitol; metal alcoholates such as zinc glycerin; amino acid metal salts such as zinc glutamate; aliphatic dibasic acids having a bicyclo structure such as bicycloheptane dicarboxylic acid or salt thereof and metal salts of such aliphatic dibasic acid; linear or cyclic hydrazide compounds; and linear and cyclic amide compounds. The nucleating agent is used at an amount of 0.001 to 10 parts by mass, more preferably at an amount of 0.01 to 5 parts by mass, with respect to 100 parts by mass of the resin.

Examples of the aforementioned flame-retardant include decabromodiphenyl ethers; halogen-based flame-retardants; phosphorous flame-retardants such as red phosphorus, ammonium phosphates, ammonium polyphosphate, melamine phosphate, melamine pyrophosphate, melamine polyphosphate, piperazine phosphate, piperazine pyrophosphate, piperazine polyphosphate, triphenyl phosphate, resorcinol.phenol.phosphoric acid condensate, resorcinol.2,6-dimethylphenol.phosphoric acid condensate, bisphenol A.phenol.phosphoric acid condensate, biphenol.phenol.phosphoric acid condensate, naphthalenediol.phenol.phosphoric acid condensate, pentaerythritol.phenol.phosphoric acid condensate, 1,3-diaminomethylbenzene.phenol.phosphoric acid condensate and phosphazene compound; and metal hydroxides such as magnesium hydroxide and aluminum hydroxide. The flame-retardant is used at an amount of 0.1 to 200 parts by mass, more preferably at an amount of 1 to 100 parts by mass, with respect to 100 parts by mass of the resin.

Examples of the aforementioned flame-retardant aid include inorganic compounds such as magnesium hydroxide, antimony trioxide and talc, and surface-treated products thereof; melamine cyanurate; pentaerythritol; silicone compounds; and polytetrafluoroethylene.

Examples of the aforementioned heavy-metal inactivator include salicylamide-1,2,4-triazol-3-yl, bis-salicylic acid hydrazide, dodecanedioyl bis(2-(2-hydroxybenzoyl)hydrazide) and bis(3-(3,5-di-t-butyl-4-hydroxyphenyl)propionate)hydrazide. The heavy-metal inactivator is used at an amount of 0.001 to 10 parts by mass, more preferably at an amount of 0.05 to 5 parts by mass, with respect to 100 parts by mass of the resin.

Examples of the aforementioned antistatic agent include cationic antistatic agents such as fatty acid quaternary ammonium ion salts and quaternary polyamine salts; anionic antistatic agents such as higher alcohol phosphoric acid ester salts, higher alcohol EO adducts, polyethylene glycol fatty acid esters, anionic alkyl sulfonic acid salts, higher alcohol sulfuric acid ester salts, higher alcohol ethylene oxide adduct sulfuric acid ester salts and higher alcohol ethylene oxide adduct phosphoric acid ester salts; nonionic antistatic agents such as polyalcohol fatty acid ester, polyglycol phosphate ester and polyoxyethylene alkyl allyl ether; and amphoteric antistatic agents such as amphoteric-type alkyl betaine (e.g. betaine alkyldimethyl aminoacetate) and imidazoline-type amphoteric activator. Such antistatic agent can be used individually or two or more antistatic agents may be used in combination. The antistatic agent is used at an amount of 0.001 to 10 parts by mass, more preferably at an amount of 0.01 to 5 parts by mass, with respect to 100 parts by mass of the resin.

Examples of the aforementioned lubricant include fatty acid amides such as lauryl amide, myristyl amide, stearyl amide and behenyl amide; metallic soaps such as ethylenebisstearyl amide, polyethylene wax, calcium stearate and magnesium stearate; and metal salts of phosphoric acid esters such as magnesium distearyl phosphoric acid ester and magnesium stearyl phosphoric acid ester. The lubricant is used at an amount of 0.001 to 20 parts by mass, more preferably at an amount of 0.01 to 10 parts by mass, with respect to 100 parts by mass of the resin.

As the aforementioned metallic soap, salts of metal such as magnesium, calcium, aluminum or zinc and saturated or unsaturated fatty acid such as lauric acid, myristic acid, palmitic acid, stearic acid, behenic acid or oleic acid are used. The water content, melting point, particle diameter or the composition of the fatty acid is not restricted, and the production method may be either a double decomposition method by reaction between a fatty acid salt of alkali metal and a metal (hydro) oxide or a direct method in which a fatty acid and a metal (hydro)oxide are subjected to neutralization reaction in the presence or absence of a solvent. Further, either of such fatty acid or metal may be in excess amount. The metallic soap is used at an amount of 0.001 to 10 parts by mass, more preferably at an amount of 0.01 to 5 parts by mass, with respect to 100 parts by mass of the resin.

The aforementioned hydrotalcite may either be a natural or synthetic product, and it also may be one which is modified with alkali metal such as lithium or one whose carbonate anions are partially substituted by perchloric acid. Particularly preferred is one having a composition represented by the following Formula (4):

$$Zn_xMg_yAl_2(OH)_{2(x+y+2)}CO_3 \cdot nH_2O \qquad (4)$$

(wherein, x represents 0 to 3; y represents 1 to 6; x+y represents 4 to 6; and n represents 0 to 10), and such hydrotalcite can be used regardless of the presence or absence of crystal water and surface treatment. Further, the particle diameter is not particularly restricted; however, it is preferably as small as possible within the range in which the properties as hydrotalcite are not impaired. A larger particle diameter results in a lower dispersibility and less stabilization effect, thereby deteriorating the physical properties of the resulting resin composition, such as mechanical strength and transparency. The hydrotalcite is used at an amount of 0.001 to 10 parts by mass, more preferably at an amount of 0.005 to 5 parts by mass, with respect to 100 parts by mass of the resin.

As the aforementioned filler, glass fiber, carbon fiber, Kevler fiber, talc, silica, calcium carbonate and the like or a mixture thereof is used. These reinforcing fibers may also be either long or short filament and particularly when glass fiber filaments are used, the resin composition according to the present invention is preferred since it does not damage the glass fibers. Further, it is preferred that the filler be surface-treated in order to improve the compatibility with the resin. The filler is used at an amount of 5 to 200 parts by mass, preferably at an amount of 10 to 100 parts by mass, with respect to 100 parts by mass of the resin.

EXAMPLES

The present invention will be described concretely byway of Examples thereof; however, the present invention is not restricted thereto.

Example 1

Into a reaction vessel fitted with a stirrer, 18.4 g (0.1 mol) of cyanuric chloride represented by the aforementioned Compound No.7, 20 g (0.15 mol) of aluminum trichloride and 89.5 g of sulfolane were added and heated to 80° C. with stirring. Thereto dropped subsequently was a solution of 2-methylresorcinol represented by the aforementioned Compound No.8/sulfolane (43.4 g (0.35 mol)/67 g), and the resultant was maintained at 80° C. for 1.5 hours and allowed to react at 90° C. for 7.5 hours. To diluted hydrochloric acid at 90° C. (concentrated hydrochloric acid/water=20 g/1 L) which was prepared in advance in a reaction vessel fitted with a stirrer, the aforementioned reaction solution is slowly dropped with stirring. The thus obtained mixture is maintained at 90° C. for 1 hour to allow decomposition of aluminum chloride complex. The thus obtained product was cooled to room temperature, filtered by a suction filter and subsequently dried using a vacuum dryer to obtain light-yellow powder.

The yield was 37.2 g (83% yield) and the purity based on the area ratio obtained by HPLC (column; PEGASIL ODS manufactured by Senshu Scientific co. ltd., developing solvent; methanol: 0.3% phosphoric acid=90:10) was 91.6%. The yield of the compounds, which were believed to be the by-products below, was 7.4%.

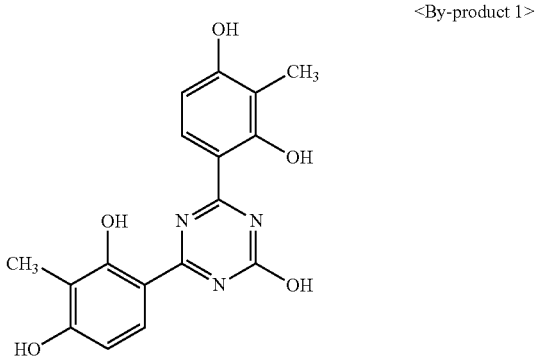

<By-product 1>

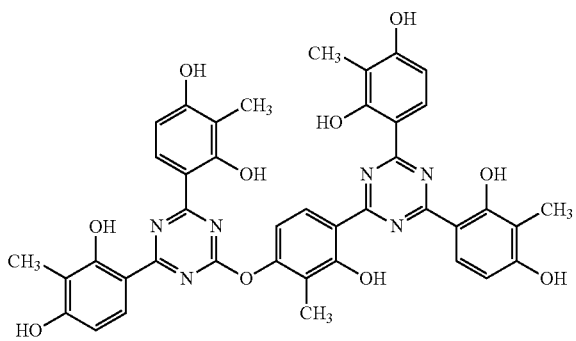

<By-product 2>

The infrared absorption spectrum of the thus obtained compound was (KBr, cm$^{-1}$) : 3364, 2924, 1612, 1542, 1501, 1423, 1300, 1080, and the $^1$H-NMR was (400 MHz, DMSO-d$_6$, ppm) : 12.65 (s, —OH), 9.49 (s, —OH), 6.82 (d, Ph), 5.76 (d, Ph), 1.24 (s, —CH$_3$); therefore, the thus obtained compound was confirmed to be the aforementioned Compound No.1.

Example 2

Light-yellow powder was obtained in the same manner as in Example 1 except that the amount of aluminum trichloride was changed to 13.6 g (0.102 mol). The yield was 43.7 g (98% yield) and the purity was 91.8%. The yield of the by-products was 4.6%.

Comparative Example 1

Yellow powder was obtained in the same manner as in Example 1 except that the solvent was changed from sulfolane to diglyme. The yield was 19.7 g (44% yield) and the purity was 29.1%. The yield of the by-products was 19.4%.

Comparative Example 2

The same procedure as in Example 1 was carried out except that the amount of aluminum trichloride was changed to 4 g (0.03 mol); however, the reaction hardly progressed.

Comparative Example 3

With the same amount of catalyst as in Comparative Example 2, the reaction temperature was increased to 120° C. to carry out the reaction. Generation of HCl was observed in association with the reaction progress. The reaction solution was treated in the same manner as in Example 1; however, obtained was not powder, but red-brown viscous substance. The purity thereof was 22% and the substance contained as its main component a by-product having a large molecular weight which is not normally observed.

Example 3

Into a reaction vessel, 18.4 g (0.1 mol) of cyanuric chloride represented by the aforementioned Compound No.7, 43.4 g (0.35 mol) of 2-methylresorcinol represented by the aforementioned No. 8, 20 g (0.15 mol) of aluminum trichloride, 340 g of chlorobenzene and 18 g of cyclopentyl methyl ether were added and allowed to react for 2 hours. Thereto added at 80° C. was 80 g of 6N hydrochloric acid, and the thus obtained mixture was heated to 90° C. to allow decomposition of aluminum chloride complex for 1 hour. Subsequently, 200 g of toluene was added and the resultant was reflux-dehydrated for 2 hours. The thus reflux-dehydrated mixture was cooled and then filtered using a Buchner funnel to obtain light-yellow powder. The yield was 42.5 g (95% yield) and the purity based on the area ratio obtained by HPLC (column; Jordi-Gel DVB 100A manufactured by Jordi Associates, Inc., developing solvent; tetrahydrofuran (THF)) was 99%. Further, the yield of the compound believed to be By-product 1 was 1%.

The infrared absorption spectrum of the thus obtained compound was (KBr, cm$^{-1}$): 3364, 2924, 1612, 1542, 1501, 1423, 1300, 1080, and the $^1$H-NMR was (400 MHz, DMSO-$d_6$, ppm): 12.65 (s, —OH), 9.49 (s, —OH), 6.82 (d, Ph), 5.76 (d, Ph), 1.24 (s, —CH$_3$); therefore, the thus obtained compound was confirmed to be the aforementioned Compound No. 1.

Example 4

Light-yellow powder was obtained in the same manner as in Example 3 except that the amounts of chlorobenzene and cyclopentyl methyl ether were changed to 322 g and 36 g, respectively. The yield was 43.4 g (97% yield) and the purity was 89%. The yield of By-product 1 was 11%.

Example 5

Light-yellow powder was obtained in the same manner as in Example 3 except that the reaction temperature and the reaction time were changed to 40° C. and 9 hours, respectively. The yield was 42.1 g (94% yield) and the purity was 95%. The yield of By-product 1 was 5%.

Comparative Example 4

When it was tried to raise the temperature to 80° C. in order to carry out the reaction in the same manner as in Example 3 except that the solvent was changed to 358 g of chlorobenzene (without cycloalkyl alkyl ether), a drastic exothermic reaction occurred, increasing the temperature to 133° C. The thus obtained product was in the form of red oily viscous substance. The yield was 23.3 g (52% yield) and the purity was 53%. The yields of By-product 1 and By-product 2 were 23% and 24%, respectively.

Comparative Example 5

Orange powder was obtained in the same manner as in Example 3 except that diglyme was used in place of cyclopentyl methyl ether. The yield was 26.0 g (58% yield) and the purity was 82%. The yield of By-product 1 was 18%.

Comparative Example 6

Red oily viscous substance was obtained in the same manner as in Example 3 except that tetrahydrofuran was used in place of cyclopentyl methyl ether and the reaction temperature was changed to 40° C. The yield was 17.0 g (38% yield) and the purity was 41%. The yield of By-product 1 was 59%.

Comparative Example 7

Red oily viscous substance was obtained in the same manner as in Example 3 except that the solvent was changed to 224 g of diglyme (without chlorobenzene/cycloalkyl alkyl ether). The yield was 20.6 g (46% yield) and the purity was 51%. The yields of By-product 1 and By-product 2 were 17% and 32%, respectively.

From the results of Example 1 and Comparative Example 1, it is seen that the use of sulfolane solvent as in the case of the present invention enables to suppress the generation of by-products, which was difficult to control with conventionally used solvents, and that the present invention can provide a production method in which the yield and purity of the obtained product is superior. In addition, from Examples 1 and 2, as well as Comparative Example 2, it is apparent that the triazine compound can be produced at a high yield and high purity only with the amount of catalyst in the range of the present invention. Further, the present invention can produce the desired product at a high yield and high purity using a Lewis acid only at an amount of approximately half of what is generally required in a Friedel-Crafts reaction; therefore, it is an industrially valuable production method which generates only a small amount of waste materials. Furthermore, in Examples 1 and 2, the triazine compound was easily produced and purified without rapid solidification or the like.

From Examples 3 to 5 and Comparative Examples 4 to 7, it is seen that a high yield was not attained when using an ether-based solvent other than the one used in the present invention and that the triazine compound was obtained at a high yield and high purity with the generation of by-products being suppressed only in those cases of Examples 3 to 5 in which cycloalkyl alkyl ether solvent was used. It is clear that, by the present invention, the triazine compound can be produced at a high purity and high yield. Further, in Examples 3 to 5, the triazine compound was easily produced and purified without rapid solidification or the like.

The invention claimed is:

1. A method of producing 2,4,6-tris(hydroxphenyl)-1,3,5-triazine compound represented by the following Formula (1):

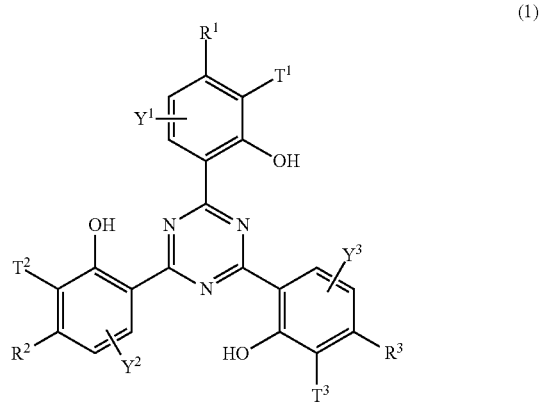

(wherein,

R$^1$, R$^2$ and R$^3$ are identical and represent a hydrogen atom, hydroxyl group or C$_1$-C$_4$ alkyl group;

T$^1$, T$^2$ and T$^3$ are identical and represent a hydrogen atom, C$_1$-C$_4$ alkyl group or C$_2$-C$_4$ alkenyl group; and Y$^1$, Y$^2$ and Y$^3$ are identical and represent a hydrogen atom or C$_1$-C$_4$ alkyl group), wherein the reaction between cyanuric halide compound represented by the following Formula (2):

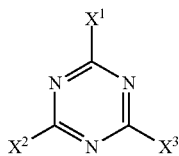
(2)

(wherein,
$X^1$ represents a halogen atom; and
$X^2$ and $X^3$ each independently represent a halogen atom or a substituent by which hydrogen atom of the phenyl ring of the compound represented by the following Formula (3) is substituted)
and hydroxyphenyl compound represented by the following Formula (3):

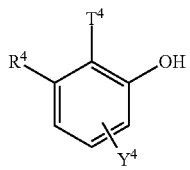
(3)

(wherein,
$R^4$ represents a hydrogen atom, hydroxyl group or $C_1$-$C_4$ alkyl group;
$T^4$ represents a hydrogen atom, $C_1$-$C_4$ alkyl group or $C_2$-$C_4$ alkenyl group; and
$Y^4$ represents a hydrogen atom or $C_1$-$C_4$ alkyl group)
is carried out by using, as the reaction solvent, a solvent containing sulfolane as the main component in the presence of a catalyst consisting essentially of a Lewis acid at an amount of 0.3 to 0.7 equivalent with respect to 1 equivalent of halogen atom of the cyanuric halide compound represented by said Formula (2), or by using a mixed solvent of inert solvent and the cyclopentyl alkyl ether represented by the following Formula (4):

$$Z^1-O-Z^2 \qquad (4)$$

(wherein,
$Z^1$ represents a cyclopentyl group which optionally has a substintent(s); and
$Z^2$ represents a $C_1$-$C_4$ alkyl group which optionally has a substituent(s)).

2. The method of producing 2,4,6-tris(hydroxyphenyl)-1,3,5-triazine compound according to claim 1, wherein said solvent containing sulfolane as the main component is used and in said Formulae (1) and (3), $R^1$ to $R^4$ are a hydroxyl group, $T^1$ to $T^4$ are a hydrogen atom or methyl group, and $Y^1$ to $Y^4$ are a hydrogen atom.

3. The method of producing 2,4,6-tris(hydroxyphenyl)-1,3,5-triazine compound according to claim 1, wherein said solvent containing sulfolane as the main component is used and said $T^1$ to $T^4$ are a methyl group.

4. The method of producing 2,4,6-tris(hydroxyphenyl)-1,3,5-triazine compound according to claim 1, wherein said solvent containing sulfolane as the main component is used and $X^1$ to $X^3$ in said Formula (2) are a chlorine atom.

5. The method of producing 2,4,6-tris(hydroxyphenyl)-1,3,5-triazine compound according to claim 1, wherein said Lewis acid is aluminum trichloride.

6. The method of producing 2,4,6-tris(hydroxyphenyl)-1,3,5-triazine compound according to claim 1, wherein the amount of said Lewis acid is 0.4 to 0.5 equivalent with respect to 1 equivalent of halogen atom of said cyanuric halide compound.

7. The method of producing 2,4,6-tris(hydroxyphenyl)-1,3,5-triazine compound according to claim 1, wherein said solvent containing sulfolane as the main component is used and the reaction temperature is 60 to 100° C.

8. The method of producing 2,4,6-tris(hydroxyphenyl)-1,3,5-triazine compound according to claim 1, wherein said mixed solvent of inert solvent and cyclopentyll alkyl ether represented by said Formula (4) is used and in said Formulae (1) and (3), $R^1$ to $R^4$ are a hydroxyl group, $T^1$ to $T^4$ are a hydrogen atom or methyl group, and $Y^1$ to $Y^4$ are a hydrogen atom.

9. The method of producing 2,4,6-tris(hydroxyphenyl)-1,3,5-triazine compound according to claim 1, wherein said mixed solvent of inert solvent and cyclopentyl alkyl ether represented by said Formula (4) is used and said $T^1$ to $T^4$ are a methyl group.

10. The method of producing 2,4,6-tris(hydroxyphenyl)-1,3,5-triazine compound according to claim 1, wherein said mixed solvent of inert solvent and cyclopentyl alkyl ether represented by said Formula (4) is used and $X^1$ to $X^3$ in said Formula (2) are a chlorine atom.

11. The method of producing 2,4,6-tris(hydroxyphenyl)-1,3,5-triazine compound according to claim 1, wherein said inert solvent is at least one selected from the group consisting of chlorobenzene, dichlorobenzene, trichlorobenzene, bromobenzene, dibromobenzene and tribromobenzene.

12. The method of producing 2,4,6-tris(hydroxyphenyl)1,3,5-triazine compound according to claim 1, wherein $Z^1$ and $Z^2$ in said Formula (4) are a cyclopentyl group and a $C_1$-$C_4$ alkyl group, respectively.

13. The method of producing 2,4,6-tris(hydroxyphenyl)-1,3,5-triazine compound according to claim 1, wherein the mass ratio of said inert solvent to said cyclopentyl alkyl ether is 50:50 to 99:1.

* * * * *